US009134303B1

(12) United States Patent
Koulchin et al.

(10) Patent No.: US 9,134,303 B1

(45) Date of Patent: Sep. 15, 2015

(54) **ICT IMMUNOASSAY FOR *LEGIONELLA PNEUMOPHILA* SEROGROUP 1 ANTIGEN EMPLOYING AFFINITY PURIFIED ANTIBODIES THERETO**

(75) Inventors: Vladimir Andrei Koulchin, Portland, ME (US); Norman James Moore, North Berwick, ME (US); Elena Valentin Molokova, Portland, ME (US)

(73) Assignee: Alere Scarborough, Inc., Scarborough, ME (US)

( * ) Notice: Subject to any disclaimer, the term of this patent is extended or adjusted under 35 U.S.C. 154(b) by 0 days.

(21) Appl. No.: 09/139,720

(22) Filed: Aug. 25, 1998

(51) Int. Cl.

| | |
|---|---|
| ***C12Q 1/68*** | (2006.01) |
| ***G01N 33/00*** | (2006.01) |
| ***G01N 33/569*** | (2006.01) |
| ***C12M 3/00*** | (2006.01) |
| ***G01N 33/53*** | (2006.01) |

(52) U.S. Cl.
CPC .................................... *G01N 33/53* (2013.01)

(58) Field of Classification Search
CPC .............. C12Q 1/00; C12Q 1/02; C12Q 1/06; C12Q 2537/125; G01N 33/53; G01N 33/5302; G01N 33/54306; G01N 33/54366; G01N 33/558; G01N 33/566; G01N 33/569; G01N 33/6854
USPC ......... 435/4, 5, 71, 7.32, 283.1, 286.5, 287.1, 435/287.2, 287.9, 288.3, 288.5, 288.7, 69.3, 435/340, 7.1; 436/164, 166, 501, 506, 513, 436/529, 536, 543, 512, 518, 523, 525, 532, 436/538, 540, 547, 824; 424/234.1; 530/387 J, 388.4, 413, 417
See application file for complete search history.

(56) References Cited

U.S. PATENT DOCUMENTS

| | | | | |
|---|---|---|---|---|
| 4,206,094 | A * | 6/1980 | Yen et al. | 260/8 |
| 4,373,932 | A | 2/1983 | Gribnau et al. | |
| 4,411,832 | A * | 10/1983 | Cuatrecasas et al. | 260/121 |
| 4,514,509 | A * | 4/1985 | Kohler et al. | 436/518 |
| 4,703,017 | A | 10/1987 | Campbell et al. | |

(Continued)

FOREIGN PATENT DOCUMENTS

| | | |
|---|---|---|
| EP | 497524 A2 | 8/1992 |
| JP | 1032169 | 8/1977 |

(Continued)

OTHER PUBLICATIONS

Barthe et al. 1988. J. of Clin. Microbio. 26(5):1016-1023, 1988.*

(Continued)

*Primary Examiner* — Ja'Na Hines
(74) *Attorney, Agent, or Firm* — Foley Hong LLP

(57) ABSTRACT

The present invention involves extracting from *Legionella* bacteria, particularly *L. pneumophila* bacteria, an essentially protein-free O-polysaccharide or carbohydrate antigen, coupling this antigen to an activated chromatographic column through a protein spacer molecule which is first conjugated to the antigen, utilizing the column thus prepared for the affinity purification of raw polyvalent antibodies to the same *Legionella* bacterium from which the O-polysaccharide or carbohydrate antigen was separated—thereby obtaining antigen-specific antibodies which are useful for the rapid detection of the corresponding *Legionella* bacterium or its antibody in human bodily fluids such as urine, sputum, blood and the like or in environmental samples suspected of harboring the *Legionella* bacterium.

7 Claims, 2 Drawing Sheets

(56) References Cited

U.S. PATENT DOCUMENTS

| | | | | |
|---|---|---|---|---|
| 4,751,190 | A | 6/1988 | Chiapetta et al. | |
| 4,780,407 | A * | 10/1988 | Strosberg et al. | 435/7 |
| 4,861,711 | A | 8/1989 | Friesen et al. | |
| 4,888,279 | A | 12/1989 | Zeiger | |
| 4,943,522 | A | 7/1990 | Eisinger et al. | |
| 5,059,591 | A | 10/1991 | Janoff et al. | |
| 5,149,622 | A | 9/1992 | Brown et al. | |
| 5,367,058 | A | 11/1994 | Pitner et al. | |
| 5,415,994 | A * | 5/1995 | Imrich et al. | 435/5 |
| 5,455,032 | A | 10/1995 | Kenny et al. | |
| 5,455,302 | A | 10/1995 | Saito et al. | |
| 5,536,646 | A | 7/1996 | Sand et al. | |
| 5,571,511 | A | 11/1996 | Fischer | |
| 5,602,040 | A * | 2/1997 | May et al. | 436/514 |
| 5,623,057 | A | 4/1997 | Marburg et al. | |
| 5,665,561 | A | 9/1997 | Tuomanen et al. | |
| 5,695,768 | A | 12/1997 | Malcolm | |
| 5,773,007 | A | 6/1998 | Penney et al. | |
| 5,807,715 | A | 9/1998 | Morrison et al. | |
| 5,847,112 | A | 12/1998 | Kniskern et al. | |
| 5,871,951 | A | 2/1999 | Weiser | |
| 5,879,881 | A | 3/1999 | Rubenstein | |
| 5,948,900 | A | 9/1999 | Yother et al. | |
| 6,010,910 | A | 1/2000 | Radcliffe et al. | |
| 6,057,421 | A | 5/2000 | Muller et al. | |
| 6,194,221 | B1 | 2/2001 | Rehg et al. | |
| 6,217,866 | B1 | 4/2001 | Schlessinger et al. | |
| 6,245,335 | B1 | 6/2001 | Masure et al. | |
| RE37,437 | E | 11/2001 | Friesen et al. | |
| 6,495,139 | B2 | 12/2002 | Tuomanen et al. | |
| 6,566,500 | B1 | 5/2003 | Vitetta et al. | |
| 6,824,997 | B1 | 11/2004 | Moore et al. | |
| 2002/0015693 | A1 | 2/2002 | Metzger et al. | |
| 2003/0157115 | A1 | 8/2003 | Bay et al. | |
| 2004/0247605 | A1 | 12/2004 | Kokai-Kun et al. | |
| 2009/0186368 | A1 | 7/2009 | Raven et al. | |

FOREIGN PATENT DOCUMENTS

| | | | |
|---|---|---|---|
| JP | 1503174 | | 10/1989 |
| JP | 3176659 | | 7/1991 |
| JP | 2001502046 | | 2/2001 |
| WO | WO-88/08534 | A1 | 11/1988 |
| WO | WO-9210936 | A1 | 7/1992 |
| WO | WO-92/21977 | A1 | 12/1992 |
| WO | WO-9400149 | A1 | 1/1994 |
| WO | WO-9412641 | A1 | 6/1994 |
| WO | WO-00/16803 | | 3/2000 |
| WO | WO-2009/122714 | A1 | 10/2009 |

OTHER PUBLICATIONS

Ciesielski et al. 1986. Infect. and Immun. 51(2): 397-404, 1986.*
Jurgens et al. 1995. Infect. and Immun. 63(6): 2180-2184, 1995.*
Kazandjian et a1.1997. J. of Clin. Microbio. 35(4): 954-956, 1997.*
Knirel et al. 1994. Eur. J. Biochem. 221: 239-245, 1994.*
Nolte et al. 1986. infect. and Immun. 52(3): 676-681, 1986.*
Barthe et al. 1988. J. of Clin. Micro. vol. 26(5): 1016-1023.*
Ciesielski et al. 1986. Infect and Immun. vol. 51(2): 397-404.*
Kazandjian et al. 1997. J. of Clin. Microbio. vol. 35(4): 954-956.*
Knirel et al. 1994. Eur. J. Biochem. vol. 221: 239-245.*
Helbig et al. 1997. J. Clin. Microbio. vol. 35(11): 2841-2845.*
Dominguez et al. 1998. J. Clin. Microbio. vol. 36(9): 2718-2722.*
Bibb et al. 1984. J. Clin. Microbio. vol. 20(3): 478-482.*
Kohler et al. 1981. Annals of Internal Medicine. Vo. 94(5):601-605.*
Binax NOW Legionella Urinary Antigen Test, Product Instructions.*
Binax Legionella Urinary Antigen EIA, Product Instructions.*
Kazandjian et al. 1997. J. Clin.Microbio. vol. 35(4): 954-956.*
Bibb et al. 1984. J. of Clin. Microbio. vol. 20(3):478-482.*
Dec. 1, 1977, Fraser et al., "Legionnaires Disease", 297 New Eng. J. of Medicine, 1189-1197.
Apr. 1979, Tilton, R.C., Legionnaires' Disease Antigen Detected by Enzyme-Linked Immunosorbent Assay, 90 Annals of Internal Medicine, 697-698.
May 1979, Berdal et al. , "Detection of *Legionella Pneumophila* Antigen in Urine by Enzyme-Linked Immunospecific Assay", A.J. Clin. Microbiol., 575-578.
May 1981, Kohler et al., "Rapid Radioimmunoassay Diagnosis of Legionnaires' Disease", 94 Annals of Internal Medicine, 601-605.
May 1981, Mangiafico et al., "Rapid and Sensitive Method for Quantitation of *Legionella Pneu-mophila* Serogroup 1 Antigen from Human Urine", 13 J. Clin. Microbiol., 843-845.
Feb. 1982, Flesher et al., "Isolation of a Serogroup 1-Specific Antigen from *Legionella Pneumophila*", 145 J. of Infectious Diseases, 224-223.
Apr. 1982, SathapataYabongs, B. et al., "Rapid Diagnosis of Legionnaires' Disease by Urinary Antigen Detection", 72 Am. J. of Medicine, 576-582.
Jun. 1982, Tang et al., Detection of *Legionella* Antigeneuria by Reverse Passive Agglutination, 15 J. Clin. Microbiol., 998-1000.
Oct. 1983, Guillet, J. G. et al., "Characterization, Serological Specificity and Diagnostic Possibilities of Monoclonal Antibodies Against *Legionella Pneumophila*", 18 J.Clin. Microbiol., 793-797.
Nov. 1983, Thacker et al., "Comparison of Slide Agglutination Test and Direct Imunoflorescence Assay for Identification of *Legionella* Isolates", 18 J.Clin. Microbiol., 1113-1118.
May 1984, Reingold, A.L. et al., *Legionella Pneumonia* in the United States: The Distribution of Serogroups and Species Causing Human Illness, 149 J. Infectious Disease, 819.
Sep. 1984, Bibb, W.F. et al., "Detection of *Legionella Pneumophila* Antigens in Serum and Urine Specimens by Enzyme-Linked Immunosorbent Assay with Monoclonal and Polyclonal Antibodies", 20 J. Clin. Microbiol., 478-482.
Oct. 1984, Kohler, R.B. et al., "Onset and Duration of Urinary Antigen Excretion in Legionnaires' Disease", 20 J. Clin. Microbiol., 605-607.
1986, Kohler, R.B., "Antigen Detection for the Rapid Diagnosis of Mycoplasma and *Legionella Pneumonia* ", 4 Diagnosis Microbiol. Infect. Disease, 47S-59S.
Feb. 1986, Ciesielski, C.A. et al., "Serogroup Specificity of *Legionella Pneumophila* Is Related to Lipopolysaccharide Characteristics", 51 Infection and Immunity, 397-404.
Jun. 1986, Nolte, F.S. et al., "Electrophoretic and Serological Characterization of the Lipo-polysaccharides of *Legionella Pneumophila*", 53 Infection and Immunity, 676-681.
Sep. 1986, Otten, S. et al., "Stereospecific Antigens of *Legionella Pneumophila*", 167 J. Bacteriology, 893-904.
Oct. 1986, Tang, P.W. et al., "Broad-Spectrum Enzyme-Linked Immunosorbent Assay for Detection of *Legionella* Soluble Antigens", 24 J. Clin. Microbiol., 556-558.
1986-1987, Tang, P.W. et al., "*Legionella Antigenuria*: Six Year Study of Broad Spectrum Enzyme-Linked Immunosorbent Assay as a Routine Diagnostic Test", [journal unknown], 12-13.
May 1988, Barthe, C. et al., Common Epitope on the Lipopolysaccharide of *Legionella Pneu-mophila* Recognized by a Monoclonal Antibody, 26 J. Clin. Microbiol., 1016-1023.
1989, Helbig, J.H. et al., "Diagnostek von Legionella-Pneumonien durch Nachweis der Antigenurie mittels Enzymimmunoassay unter Verwendung von 6 unterschiedlichen Antikörperspezifitäten",35 Z. Gesamte Hyg., 591-593 [in Germ. with Eng. Abstract].
Dec. 1990, Ruf, B. et al., "Prevalence and Diagnosis of *Legionella Pneumonia*: A 3-Year Pro-spective Study with Emphasis on Application of Urinary Antigen Detection", 162 J. of Infectious Diseases, 1341-1348.
Feb. 1991, Roig, J. et al., "Comparative Study of *Legionella Pneumophila* and Other Noso-comial-Acquired Pneumonias", 99 Chest, 344-350.
Oct. 1991, Leland, D.S. et al., "Evaluation of the L-CLONE *Legionella Pneumophila* Sero-group 1 Urine Antigen Test", 29 J. Clin. Microbiol., 2220-2223.
Jan. 1992, Stout, J.E. et al., "Potable Water As a Cause of Sporadic Cases of Community-Acquired Legionnaires' Disease", 326 New Eng. J. of Medicine, 151-155.
1993, Edelstein, P.H., "Legionnaires' Disease", 16 Clin. Infectious Diseases, 741-749.

(56) References Cited

OTHER PUBLICATIONS

1993, Edelstein, P.H., "Laboratory Diagnosis of Legionnaires Disease: An Update from 1984", State of the Art Lecture; journal unknown.
Feb. 1994, Ramirez, J.A. et al., Rapid Tests for the Diagnosis of *Legionella* Infections, 92 KMA Journal, 62-65.
Nov. 14, 1994, Marston, B.J. et al., "Surveillance for Legionnaires' Disease", 154 Arch. Intern. Med., 2417-2422.
1994, Knirel, Y.A. et al., The Structure of the O-Specific Chain of *Legionella Pneumophila* Serogroup 1, 221 Eur. J. Biochem., 239-245.
1994, Caratula, J. et al., "Risk Factors for Nosocomial *Legionella Pneumophila* Pneumonia", 149 Am. J. Resp. Crit. Care Med., 625-629.
1995, Plouffe, J.F. et al., "Reevaluation of the Definition of Legionnaires' Disease: Use of the Urinary Antigen Assay", 20 Clin. Infectious Diseases, 1286-1291.
Jun. 1995, Jurgens, D. et al., "Cross-Reacting Lipopolysaccharide Antigens in *Legionella Pneumophila* Serogroups 1 to 14", 63 Infection and Immunity, 2180-2184.
Aug. 1995, Ta, A.C. et al., "Comparison of Culture Methods for Monitoring *Legionella* Species in Hospital Potable Water Systems and Recommendation for Standardization of Such Methods", 33 J. Clin. Microbiol., 2118-2123.
1995, Keller, D.W. et al., "Community Outbreak of Legionnaires' Disease: An Investigation Confirming the Potential for Cooling Towers to Transmit *Legionella* Species", 22 Clinical Infectious Diseases, 257-261.
1996, Murdoch, D.R. et al., "Use of the Polymerase Chain Reaction to Detect *Legionella* DNA in Urine and Serum Samples from Patients with Pneumonia", 23 Clin. Infectious Diseases, 475-480.
Jun. 1996, Hackman, B.A. et al., Comparison of Binax Legionella Urinary Antigen EIA Kit with Binax RIA Urinary Antigen Kit for Detection of *Legionella Pneumophila* Serogroup I Antigen, 34 J. Clin. Microbiol., 1579-1580.
Apr. 1997, Kazandjian, D. et al., Rapid Diagnosis of *Legionella Pneumophila* Serogroup I Infection with the Binax Enzyme Immunoassay Urinary Antigen Test, 35 J. Clin. Microbiol., 954-957.
Sep. 1997, Stout, J.E. et al., "Legionellosis", 337 New Eng. J. Medicine, 682-687.
Horwitz, M.A. et al., "Prospects for Vaccine Development", Presented at 4th Int'l Symposium on Legionella, In Barbaree, J.M., Breiman, R.F. & DuPour, A.P. (Eds.) *Legionella* (1993) (2 pages).
1993 or 1994, "Legionnaires's Disease" (excerpt from a textbook; author anonymous) (5 pages).
Mar. 26, 1996, Author Anonymous, "Bacterial Pneumonia Part I. Issues on Prevention of Nosocomial Pneumonia, 1994"—Excerpt from CDC On-Line Guidelines (15 pages titled "Bacterial Pneumonia").
More, N. (sic Moore, N.), Molokova, E. and Koulchin, V., Abstract C4-33, American Society for Microbiology Meeting May 17-21, 1998 entitled Development of an Immunochromatographic (ICT) Assay for Identification of *Legionella Pneumophila*.
Moore, N.; Chute, A. & Koulchin, V., Abstract Development of Immunosorbent (ELISA)and Immunochromatographic (ICT) Assays for the Detection of Food-Borne Patrogen *E. coli* 0157:H7, Poster presented at American Society for Microbiology Meeting, New Orleans, 1996.
Pavlova, I.S., Lukin, Y.V., Avdeev, D.W. and Kulshin, V.A., "Non-Instrumental Immunoassay based on Coloured Polyacrolein Latex: Application to Group Specific Polysaccharide of *Streptococcus* pyogenes", *Journal of Immunoassay* 16 (2), pp. 199-212 (1995).
Pavlova, I.S., Lukin, Y.V., Kovalenko, V.A., Avdeev, D.N. Kulshin, V.A. and Zubov, V.P., *Article, Bioorganisches Kaya Khimiya*, vol. 20, No. 7 pp. 731-739 (1994) (in Russian language with English abstract on p. 739)entitled "Non-Instrumental Immunoassay Based on Coloured Polyacrolein Latex: Application to Group-Specific Polysaccharide of *Streptococcus* pyrogenes".
Weiner, M.J. and Stephen, M. "Immunodiagnosis of Systemic Aspergillosis I. Antigenemia detected by Radio immunoassay in Experimental Infection", *J. Lab. Clin. Med.* article published Jan. 1979 vol. 93 (1) pp. 111-119; (abstract only).
Bennett, Larry G., et al.; "Binding studies with antibodies having phosphorylcholine specificity and fragments derived from their homologous *streptococcus pneumoniae* type 27 capsular polysaccharide," Journal of Immunology 122(6):2356-2362 (Jun. 1979).
Bromberg, K, et al.; "Pneumococcal C and type polysaccharide detection in the concentrated urine of patients with bacteremia," Med Microbiol Immunol 179:335-338 (1990).
Brundish, et al.; "The Characterization of Pneumococcal C-Polysaccharide as a Ribitol Teichoic Acid," Biochem. J. 105:30c-31c (1967).
Chu, C, et al.; "Further Studies on the Immunogenicity of *Haemophilus influenzae* Type b and Pneumococcal Type 6A Polysaccharide-Protein Conjugates," Infection and Immunity 40(1):245-256 (Apr. 1983).
Clinical Microbiology, 25(1):29-33 (1998).
Gillespie, SH et al., "Detection of C-polysaccharide in serum of patients with *Streptococcus pneumoniae* bacteraemia," J. Clin. Pathol. 48:803-806 (1995).
Gillespie, SH et al, "Diagnosis of *Streptococcus pneumoniae* by quantitative enzyme linked immunosorbent assay of C-polysaccharide antigen," J. Clinical Pathology, 47:749-751 (Aug. 1994).
Gillespie, SH, "The diagnosis of *Streptococcus pneumoniae* infections," Reviews in Medical Microbiology 5(4):224-232 (1994).
Gotschlich, Emily C. et al., "Structural and Immunological Studies on the Pneumococcal C Polysaccharide," The Journal of Biological Chemistry 242(3):463-470 (Feb. 10, 1967).
Havas, H. Francis, et al.; "Effect of TEPC-183 Plasmacytoma on Resistance of Passively or Actively Immunized BALB/c Mice to Infection with *Streptococcus pneumoniae*," Cancer Research 44:3299-3302 (Aug. 1984).
Heymann, H., et al., "Structure of Streptococcal Cell Walls," The Journal of Biological Chemistry 238(2):502-509 (Feb. 1963).
Holmberg, H et al, "Detection of C Polysaccharide in *Streptococcus pneumoniae* in the Sputa of Pneumonia Patients by an Enzyme-Linked Immunosorbent Assay," J. Clinical Microbiology 22(1):111-115 (Jul. 1985).
Jurgens, D. et al., "Identification of *Legionella* Species by Lipopolysaccharide Antigen Pattern," J. Clin. Microbiol., 35(12):3054-3057 (1997).
Kasahara, Y., et al., "Simple devices and their possible application in clinical laboratory downsizing," Clinica Chimica Acta 267(1):87-102 (1997).
Koskela, M., et al., "Enzyme Immunoassay for Detection of Immunoglobulin G (IgG), IgM, and IgA Antibodies against Type 6B Pneumococcal Capsular Polysaccharide and Cell Wall C Polysaccharide in Chinchilla Serum," Journal of Clinical Microbiology 30(6):1485-1490 (Jun. 1992).
Krook, Aud et al, "Pneumococcal Antigens in Sputa: ELISA for the Detection of Pneumococcal C-Polysaccharide in Sputa from Pneumonia Patients," Diagn. Microbiol. Infect. Dis. 7:73-75 (1987).
Laferriere, CA et al, "The synthesis of *Streptococcus pneumoniae* polysaccharide-tetanus toxoid conjugates and the effect of chain length on immunogenicity," Vaccine 15(2):179-186 (Feb. 1997).
Liu, TY, et al., "The Chemical Composition of Pneumococcal C-Polysaccharide," The Journal of Biological Chemistry 238(6):1928-1934 (Jun. 1963).
Parkinson, Alan J., et al., "Quantitation of Pneumococcal C Polysaccharide in Sputum Samples from Patients with Presumptive Pneumococcal Pneumonia by Enzyme Immunoassay," Journal of Clinical Microbiology 30(2):318-322 (Feb. 1992).
Petitjean, F. et al., "Isolation, Purification and partial Analysis of the Lipopolysaccharide Antigenic Determinant Recognized by a Monocolonal Antibody to *Legionella Pneumophila* Serogroup 1," Res. Microbiol., 141(9):1077-1094 (1990).
Poxton, Ian R., et al., "The Structure of C-Polysaccharide from the Walls of *Streptococcus pneumoniae*," Biochem. J. 175:1033-1042 (1978).
Rosen, IA et al, "Antibodies to pneumococcal polysaccharides in human milk: lack of relationship to colonization and acute otitis media," Pediatr Infect Dis J. 15(6):498-507 (Jun. 1996).

(56) References Cited

OTHER PUBLICATIONS

Schwab, John H., et al., "Immunological Studies on a C polysaccharide Complex of Group A Streptococci Having a Direct Toxic Effect on Connective Tissue," J. of Experimental Medicine, pp. 295-307 (1959).
Sippel, JE et al, "Detection of Neisseria meningitidis Group A, *Haemophilus influenzae* Type b, and *Streptococcus pneumoniae* Antigens in Cerebrospinal Fluid Specimens by Antigen Capture Enzyme-Linked Immunosorbent Assays," J. Clin. Microbiology 20(2):259-265 (Aug. 1984).
Sjogren, et al.; "A highly specific two-site ELISA for pneumococcal C-polysaccharide using monoclonal and affinity-purified polyclonal antibodies," J Immunol Methods 102(1):93-100 (Aug. 24, 1987).
Sjogren, AM et al, "Etoilogic Diagnosis of Pneumonia by Antigen Detection: Crossreactions Between Pneumococcal C-Polysaccharide and Oral Microorganisms," Diagnostic Microbiology and Infectious Disease 6(3):239-248 (Mar. 1987).
Skerra, A, et al., "Assembly of a Functional Immunoglobulin Fv Fragment in *Escherichia coli*," Science 240:1038-1041 (May 20, 1988).
Skov Sorensen, et al., "Cross-Reactions between Pneumococci and Other Streptococci Due to C Polysaccharide and F Antigen," Journal of Clinical Microbiology 25(10):1854-1859 (Oct. 1987).
Skov Sorensen, "Monoclonal Phosphorylcholine Antibody Binds to Beta-Lipoprotein from Different Animal Species," Infection and Immunity 53(2): 264-266 (Aug. 1986).
Skov Sorensen, et al., "Ultrastructural Localization of Capsules, Cell Wall Polysaccharide, Cell Wall Proteins, and F Antigen in Pneumococci," Infection and Immunity 56(8):1890-1896 (1988).
Stuertz, K et al, "Enzyme Immunoassay Detecting Teichoic and Lipoteichoic Acids versus Cerebrospinal Fluid Culture and Latex Agglutination for Diagnosis of *Streptococcus pneumoniae* Meningitis," J. Clinical Microbiology 36(8):2346-2348 (Aug. 1998).
Sundberg-Kovamees, M., et al., "Interaction of the C-polysaccharide of *Streptococcus pneumoniae* with the receptor asialo-GM1," Microbial Pathogenesis 21(4):223-234 (1996).
Szu, S.C., et al, "Protection Against Pneumococcal Infection in Mice Conferred by Phosphocholine-Binding Antibodies: Specificity of the Phosphocholine Binding and Relation to Several Types," Infection and Immunity 39(2):993-999 (Feb. 1983).
Szu, S.C., et al., "Rabbit antibodies to the cell wall polysaccharide of *Streptococcus pneumoniae* fail to protect mice from lethal challenge with encapsulated pneumococci," Infection and Immunity 54(2):448-455 (Nov. 1986).
Westphal, O. et al, "Bacterial Lipopolysaccharides," Method Carbohydrate Chemistry vol. 5, pp. 83-91 (1965).
Wetherell, B., et al.; "Enzyme-Linked Immunosorbent Assay for Detection of *Haemophilus influenzae* Type b Antigen," J Clin Microbiol 11(6):573-580 (Jun. 1980).
Yolken, RH et al., "Enzyme Immunoassay for Detection of Pneumococcal Antigen in Cerebrospinal Fluid," J. of Clinical Microbiology 20(4):802-805 (Oct. 1984).
Yother, J, et al., "Protection of Mice from Infection with *Streptococcus pneumoniae* by Anti-Phosphocholine Antibody," Infection and Immunity 36(1):184-188 (Apr. 1982).
Chinese Office Action for Application No. 200510084709.5 dated Jan. 5, 2007.
Japanese Office Action for Application No. 2000-565904 dated Jul. 28, 2009.
Japanese Office Action for Application No. 2001-563134 mailed Aug. 17, 2010.
Bangsborg, J. M., et al.; "Cross-reactive *Legionella* antigens and the antibody response during infection," APMIS 99:854-865 (Apr. 2, 1991).
Bosshardt, Stephen C., et al.; "Flagella are a positive predictor for virulence in *Legionella*," Microbial Pathogenesis 23:107-112 (1997).
Jikkenhou, Seibutsukagaku 20; Methods for isolation, Purification of Polysaccharides, Experimental Methods in Biochemistry, Gakkai Syuppnan Center, 1087, pp. 19-35.
Kouza, Shin-Seikagaku Jikken, Protein I "Isolation, Purification, Nature," (Modern Experimental Biochemistry), pp. 214-216 (1990).
Leibl et al., "Separation of polysaccharide-specific human immunoglobulin G subclasses using a Protein A Superose column with a pH gradient elution system," Journal of Chromatography, 639:51-56 (1993).
Office Action in U.S. Appl. No. 11/761,255 mailed Dec. 23, 2010.
Japanese Patent Application No. 2000-573764 Office Action mailed Mar. 8, 2011.
Japanese Office Action for Application No. 2001-563134 mailed Mar. 15, 2011.
Office Action for Japanese Application No. 2011-031137 mailed Oct. 30, 2012.
Office Action in U.S. Appl. No. 11/982,410 dated Sep. 26, 2012.
Canadian Office Action for 2,427,693 dated May 23, 2013.
Office Action in U.S. Appl. No. 11/982,410 dated Apr. 10, 2013.
Office Action in U.S. Appl. No. 11/761,255 dated Jun. 18, 2013.
Office Action in U.S. Appl. No. 11/982,400 dated Jun. 20, 2013.
Benzing, et al. Specific Capsular Polysaccharide of Type 46 *Streptococcus pneumoniae* (American Type 73), Infection and Immunity, 32(3): 1024-1027 (Jun. 1981).
Brundish, et al. "Pneumococcal C-Substance, a Ribitol Teichoic Acid Containing Choline Phosphate," Biochemical Journal, 110: 573-582 (1968).
Kolkman, et al. "Carbohydrates, Lipids, and Other Natural Products: Functional Analysis of Glycosyltransferases Encoded by the Capsular Polysaccharide Biosynthesis Locus of *Streptococcus pneumniae* Serotype 14," The Journal of Biological Chemistry, 272(31): 19502-19508 (1997).
Kovacs, et al. "A Functional *dlt* Operon, Encoding Proteins Required for Incorporation of D-Alanine in Teichoic Acides in Gram-Positive Bacteria, Confers Resistance to Cationic Antimicrobial Peptides in *Streptococcus pneumoniae*," Journal of Bacteriology, 188(16): 5797-5805 (Aug. 2006).
Manjula, B.N. et al; "Affinity of horse anti-phophorylcholine antibodies for some pneumococcal polysaccharides, contribution of the polysaccharide backbone"; Immunochemistry, 15: 269-271 (1978).
Manning, James. M. "Chemistry and Metabolism of Macromolecules: Chromatographic Determination of the d-and I-Amino Acid Residues in Pneumococcal C-Polysaccharide," Journal of Biological Chemistry, 246:(9): 2926-2929 (May 10, 1971).
Nagel, et al. "Teichoic Acids in Pathogenic *Staphylococcus aureus*," Journal of Clinical Microbiology, 6(3): 233-237 (Sep. 1977).
Yang, et al. "Comparative Structural and Molecular Characterization of *Streptococcus pneumoniae* Capsular Polysaccharide Serotype 10*," Journal of Biological Chemistry, 286(41): 35813-35822 (Oct. 14, 2011).
Yother, Janet, et al. "Generation and Properties of a *Streptococcus pneumoniae* Mutant Which Does Not Require Choline or Analogs for Growth," 180(8): 2093-2101 (1998).
Office Action for U.S. Appl. No. 11/982,410 mailed Aug. 30, 2013.
Office Action for U.S. Appl. No. 11/982,410 mailed Feb. 14, 2014.
Examiners Decision of Rejection dated Jan. 13, 2015, from JP 2011-151090.
AlonsoDeVelasco, et al. "*Streptococcus pneumoniae*: Virulence Factors, Pathogenesis, and Vaccines," Microbiological Reviews, 59(4): 591-603 (Dec. 1995).
Au, C.C., et al. "Evaluation of the Role of the Pneumococcal Forssman Antigen (F-Polysaccharide) in the Cross-Serotype Protection Induced by Pneumococcal Subcellular Preparations," 31(1): 169-173 (Jan. 1981).
Coligan, John, E., et al. "A Disaccharide Hapten From Streptococcal Group C Carbohydrate That Cross-Reacts With the Forssman Glycolipid," The Journal of Immunology, 118(1): 6-11 (Jan. 1977.).
Hogg, Stephen D., et al. "Occurrence of Lipoteichoic Acid in Oral Streptococci," Int'l Journal of Systematic Bacteriology, 47(1): 62-66 (Jan. 1997).
Klein, Roger A., et al. "The aqueous solution structure of the tetrasaccharide-ribitol repeat-unit from the lipoteichoic acid of *Streptococcus pneumoniae* strain R6 determined using a combination of NMR spectroscopy and computer calculations," 256: 189-222 (1994).
Nowinski, et al. "Human Monoclonal Antibody Against Forssman Antigen," Science, 210: 537-539 (Oct. 31, 1980).

(56) References Cited

OTHER PUBLICATIONS

Sjogren, Ann Margaret, et al. "Deomonstration of Cross-reactions Between Pneumococci and α-Streptococci Using Gold-labelled Mono- and Polyclonal Antibodies and Elctron Microscopy," Diagn. Microbiol. Infect. Dis., 10: 7-21 (1988).

Waltman, II, W.D., et al. "Cross-Reactive Monoclonal Antibodies for Diagnosis of *Pneumococcal Meningitis*," Journal of Clinical Microbiology, 26(9): 1635-1640 (Sep. 1988).

Canadian Office Action for 2,427,693 dated Jul. 4, 2011.

Office Action in U.S. Appl. No. 11/982,410 dated Jan. 31, 2012.

Examiner's Decision of Rejection dated Jan. 13, 2015, from JP 2011-151090.

*Proc. Natl. Acad. Sci. USA.*, 1990, vol. 87, pp. 5858-5862, Aug. 1990, Microbiology.

Sjogren, AnnMargaret, et al. "Deomonstration of Cross-reactions Between Pneumococci and α-Streptococci Using Gold-labelled Mono- and Polyclonal Antibodies and Elctron Microscopy," Diagn. Microbiol. Infect. Dis., 10: 7-21 (1988).

* cited by examiner

ICT IMMUNOASSAY FOR *LEGIONELLA PNEUMOPHILA* SEROGROUP 1 ANTIGEN EMPLOYING AFFINITY PURIFIED ANTIBODIES THERETO

This invention relates to essentially protein-free carbohydrate, including polysaccharide, antigens separated from bacteria of the genus *Legionella*, and especially from serogroups and/or strains of *Legionella pneumophila*, including the O-polysaccharide antigen of *L. pneumophila* serogroup 1, and to the use of these antigens in the affinity purification of polyvalent antibodies to corresponding *Legionella* organisms. More particularly, the invention encompasses coupling the carbohydrate or polysaccharide antigen separated from a *Legionella* bacterium to an activated chromatographic column and using that column for affinity purification of the polyclonal antibodies to the same species, or the same serogroup of a species, of *Legionella*. The invention further encompasses the use of the affinity-purified polyvalent antibodies produced in immunochemical assays for the detection of *Legionella*-caused diseases such as Legionnaires disease and Pontiac fever in human patients and for the detection of environmental sources of *Legionella* infectious agents.

BACKGROUND

Legionnaires' disease, a pneumonia-like human infection caused by gram-negative bacteria of the genus *Legionella*, is virtually impossible to differentiate on a reliable clinical basis (involving assessment of patient symptoms without laboratory tests) from pneumonia and other similar lung infections. Because the disease may produce lung abscesses, infections in other bodily organs or bacteremia, and its mortality rate is significantly increased by delay in commencing appropriate therapy, there is a need for rapid and reliable diagnostic tests which has to date been only partially met. Stout, J. E. and Yu, V. L., "Legionellosis", 337, N. Eng. J. Med. 682-687 (1997). Efforts to develop such tests have been hampered by the fact that there are a number of *Legionella* species, at least some of which are known to have a number of distinct serogroups.

Legionnaires' disease was first recognized in the summer of 1976 and a number of techniques for detecting *Legionella* ("*L.*") *pneumophila*, which is now known to account for some 90% of cases (Stout and Yu, supra), have been developed in the interim. In general, these tests are time-consuming and incapable of identifying more than one serogroup of the 15 serogroups known so far to fall within the *L. pneumophila* species. It should be noted, however, that, as reported by Stout and Yu, supra, more than 80% of reported cases of Legionnaires' disease are attributable to *L. pneumophila* serogroup 1—a fact which makes the development of a rapid, reliable immunoassay for that entity of particular importance and has led researchers to focus on this as a priority.

The early efforts to establish the identity of the causative agent of Legionnaires' disease depended largely upon culturing the bacteria for 5 to 6 days and examining the culture microscopically. Efforts to speed up the identification process led to numerous immunochemical tests of varying sensitivity and specificity including, inter alia, the presently commercially available EQUATE™ radioimmunoassay ("RIA"), and the Binax enzyme immunoassay ("EIA"), both of which are sold in kit form by applicants' assignee, Binax, Inc. As indicated by Hackman, B. A. et al. in "Comparison of Binax *Legionella* Urinary Antigen EIA Kit with Binax RIA Urinary Antigen Kit for Detection of *Legionella pneumophila* Serogroup I Antigen", 34 *J. Clin. Microbiol.* 1579-1580 (1996), both of these assays were found to be specific for *L. pneumophila* Serogroup I antigen. The reported sensitivity of the EIA was 77%; that of the RIA was higher. The article indicates that each can be performed within "less than 3 h[ours] from beginning to end"; in Binax's own tests each requires at least 2½ hours to perform. More information about this EIA assay appears in Kazandjian, D. et al., "Rapid Diagnosis of *Legionella pneumophila* Serogroup I Infection with Binax Enzyme Immunoassay Urinary Antigen Test", 35 *J. Clin. Immunobiol.* 954-956 (1997).

BRIEF DESCRIPTION OF THE INVENTION

Perhaps the most significant advantage of the immunochromatographic test ("ICT") described herein is its ability to give a test result within a 15-minute time span for the presence or absence of *L. pneumophila* Serogroup I (or its antigen), which result is of high specificity and sensitivity. The speed with which this test can be reliably conducted to yield a result of high specificity and sensitivity is believed to be due to the strongly reactive nature of the affinity purified antibodies prepared in accordance with this invention. The superior reactive properties of these antibodies, in turn, is believed to be attributable to the use for affinity purification of the novel, essentially protein-free O-polysaccharide antigen of *L. pneumophila* serogroup 1 which is also a part of this invention.

Another ICT test has been made possible by the separation, according to this invention, of an antigen of *L. pneumophila* serogroup 5 which is of non-proteinaceous, carbohydrate nature and is common to multiple serogroups of *L. pneumophila*. The presence of such a common antigen has been suggested in the scientific literature; see e.g., Nolte, F. S. et al., "Electrophoretic and Serological Characterization of the Lipopolysaccharides of *Legionella pneumophila*", 52 *Infection and Immunity* 676-681 (1986); Otten, S. et al., "Serospecific Antigens of *Legionella pneumophila*", 167 *J. Bacteriol.* 893-904 (1986); Barthe, C. et al., "Common Epitope on the Lipopolysaccharide of *Legionella pneumophila* Recognized by a Monoclonal Antibody", 26 *J. Clin. Microbiol.* 1016-1023 (1988); Knirel, Y. A. et al., "The Structure of the O-specific Chain of *Legionella pneumophila* Serogroup I", 227 *Eur. J. Biochem.* 239-245 (1994). Heretofore there has been no clear report of any separation of such an antigen for use in developing a useful broad spectrum immuno-chemical assay.

This invention comprises the extraction from any *Legionella* bacterium, and especially from a bacterium of any of the serogroups of *L. pneumophila* of an essentially protein-free carbohydrate antigen, the preparation of a conjugate of this antigen with a spacer protein, the coupling of the conjugate to an affinity column, the use of that column for the purification of polyvalent antibodies to the corresponding *Legionella* bacterium, such as a bacterium of a serogroup of *L. pneumophila* and the use of the antibodies thus purified in an ICT immunoassay for detecting *Legionella* bacteria or their antigens, including antigens of *L. pneumophila* serogroups or their corresponding bacteria, as more specifically described hereinafter.

In particular, the invention includes the separation of an essentially protein-free O-polysaccharide antigen specific to *L. pneumophila* serogroup 1, its use in the affinity purification of the polyvalent antibody specific to the same microorganism and the use of that affinity purified antibody in an ICT immunoassay of high specificity and high sensitivity that is performable within 15 minutes.

In another embodiment, the invention includes the separation from *L. pneumophila* serogroup 5 of an essentially protein-free carbohydrate antigen, and its use in the affinity purification of the polyclonal antibody specific to the *L.*

*pneumophila* serogroup 5 antigen (i.e., an antibody that was obtained from a rabbit immunized with the said antigen); this antibody showed an ability to cross-react with antigens of the *L. pneumophila* serotypes 1, 2 and 4 in addition to the antigen of serotype 5.

DETAILED DESCRIPTION OF THE INVENTION

Figure 1:
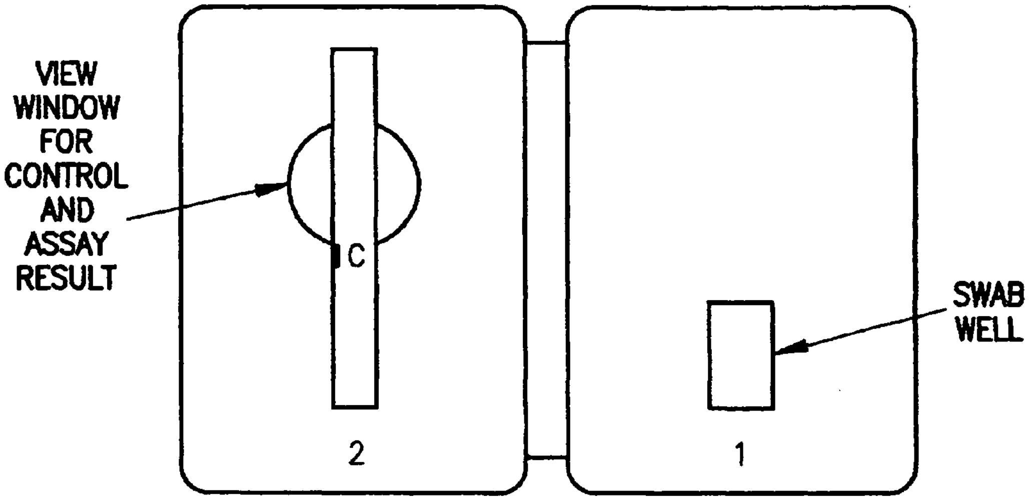
FIG. 1 and its related FIGS. 1A, 1B and 1C hereof show the structure of a typical ICT device which is suitably adapted to perform the *L. pneumophila* serogroup 1 specific assay, as described in Examples VII, VIII and IX hereof.

Previous experience in the art, including experience with the Binax RIA assay for *L. pneumophila* Serogroup 1 antigen sold under the trademark EQUATE and the Binax EIA assay for the same antigen, has shown that antigens of the *Legionella* species, including antigens of various *L. pneumophila* serogroups, are more conveniently detectable in specimens from the urine of patients infected with a *Legionella* microorganism than in specimens of blood, sputum or other fluids. This is in part because the *Legionella* antigens usually appear in urine within 1-3 days after infection of a human patient whereas their appearance at a detectable level in blood may occur later, and also in part because patients infected with Legionnaires' disease often do not produce much sputum. The ICT test which forms a part of this invention can be configured to run on blood, sputum or some other fluid such as cerebrospinal fluid, or on aqueous samples of environmental origin. It is noted that urine is generally the preferred sample fluid for diagnosis of human patients because it can be obtained non-invasively and easily, even in the doctor's office, and it si not as readily contaminated with other microorganisms, e.g., oral microflora present in sputum, which are innocuous but may affect the results obtained.

Broadly speaking, the ICT test for *L. pneumophila* serogroup 1 antigen that is specifically a part of the present invention may be designed to be run in any known disposable ICT device disclosed in the art. Preferably, the test is conducted using an ICT device of the type disclosed in copending U.S. application Ser. No. 07/706,639 now U.S. Pat. No. 6,168,956 of Howard Chandler, or one of its continuation-in part applications, all assigned to Smith-Kline Diagnostics, INC. but exclusively licensed to Binax, Inc. in a wide area of applications that includes the present diagnostic field—i.e., diseases of the respiratory system. The device is suitably impregnated with the affinity purified polyvalent antibodies herein disclosed which are specific to the antigen of *L. pneumophila* serogroup 1 antigen. Positive results of the assay are shown by the appearance of a color upon reaction of suitably labeled antibodies with the antigen. Suitable labels may be any those known in the art to produce visible color when antibodies conjugated thereto react with antigen, including finely divided metallics and various labeling material. Colloidal gold is the preferred label.

The invention contemplates that essentially protein free carbohydrate antigens may similarly be separated from each of the *Legionella* bacteria, including from bacteria of other *Legionella* species and from bacteria of other serogroups of *L. pneumophila*, that such antigens may similarly be utilized in the affinity purification of polyvalent antibodies to the corresponding *Legionella* species or serogroup bacteria and its antigen, and that these affinity-purified antibodies may be utilized in ICT and other immunoassays as specifically disclosed herein for affinity-purified antibodies to *L. pneumophila* serogroup 1.

Preliminary to the preparation of the device is obtaining the antibodies and effecting their affinity purification. The antibodies that may be used in this invention are conventional polyvalent (also called "polyclonal") antibodies obtained by the well known process of immunizing a rabbit, goat or other animal to a *Legionella* antigen, e.g., *L. pneumophila* antigen of known serogroup and bleeding the animal after the passage of an appropriate time period to obtain serum containing the desired antibodies. See, e.g., Cherry, U. B. and McKinney, R. M., pp. 91-104 in Jones, G. L. and Herbert, G. A. (Eds.), "*Legionnaires" the disease, the bacterium and the methodology*, (Center for Disease Control, Atlanta, 1979). In this invention, relative to the ICT immunoassay for *L. pneumophila* serogroup 1 disclosed herein, the rabbit or other animal is immunized to *L. pneumophila* serogroup 1 antigen and the polyvalent antibodies recovered from its blood are antibodies to *L. pneumophila* serogroup 1.

The polyvalent antibodies to be used in this invention are further subjected to affinity purification on a specially prepared chromatographic column which employs the essentially protein-free carbohydrate, including polysaccharide, antigen of the same bacterium against which the antibodies are reactive as the purifying agent for them.

Preliminary to the affinity purification of the antibodies, it is therefore necessary according to this invention to prepare an essentially protein free purified carbohydrate antigen from a culture of known *Legionella* bacteria of the desired species or serogroup of a species.

The following examples I and II explain how the purified protein free carbohydrate antigen is obtained.

EXAMPLE I

Bacteria of *L. pneumophila* Serogroup 1 (strain Philadelphia-1) were obtained from Centers for Disease Control and Prevention (Atlanta, Ga.) and cultured on charcoal-yeast extract agar plates obtained from Northeast Laboratory (Waterville, Me.) for a period of 72 hours at 37° C. Cells were harvested with phosphate-buffered saline ("PBS") at pH 7.2 containing 0.2% of $NaN_3$ and collected by centrifugation at 8000 rpm for 25 minutes. The resulting cell pellet was stored at −20° C. until used.

Wet cells from this pellet were suspended in 20 ml. 0.1 M NaOH per gram of wet cells and stirred at room temperature for 45 minutes. The pH of the solution was then adjusted with concentrated acetic acid to 3.0 and the solution was subjected to centrifugation at 8000 rpm for 20 minutes. The supernatant from this step was then neutralized with aqueous NaOH and dialyzed against distilled water.

The resulting dialyzate was concentrated 10 times on a rotary vacuum evaporator and then sonicated for 5 minutes in an ultrasonic bath.

Proteinase K, in a concentration of 0.2 mg. per ml. of the concentrated product, was added to digest the remaining proteins and the mixture was incubated at 40° C. overnight. The next step was the addition of further Proteinase K, in a concentration of 0.1 mg. Per ml., to the mixture, followed by further overnight incubation at 40° C. This second incubation was followed by concentration of the product on a rotary evaporator to a small volume, adjustment of its pH to 10-11 with 0.2% triethylamine and application of the thus-treated mixture to a column of Sephacryl S-200 from Pharmacia, equilibrated with 0.02% triethylamine. Material eluted in the first peak was pooled, adjusted with 0.1 N HCl to approximately neutral pH and dialyzed against distilled water for 18 hours followed by lyophilization.

The yield of O-polysaccharide antigen from 16.5 grams of wet cells of *L. pneumophila* serogroup 1 strain Philadelphia-1 was 62 mg.

It should be noted that in place of Proteinase K, any broad spectrum protease enzyme preparation may be used. What is important in this procedure is the elimination of protein from the antigen to the maximum possible extent within reasonable limits of time feasibility.

EXAMPLE II

Example I was repeated using *L. pneumophila* serogroup 5 strain Dallas IE as the bacteria in the culture step. 11.5 wet grams yielded 21 mg. of a carbohydrate antigen. At a later time, the procedure was again repeated, this time using *L. pneumophila* serogroup 5 (strain U8W) as the bacteria in the culture step.

It is within the scope of this invention to repeat the culturing and extraction steps as herein described on any other *Legionella* bacterium and especially on bacteria of any other of the serogroups of *L. pneumophila*, i.e., on any of serogroups 2,3,4 and 6-15 inclusive, to obtain a carbohydrate antigen essentially free of proteinaceous material.

In order to couple the essentially protein free O-polysaccharide product of Example 1 or the carbohydrate of Example II to a chromatographic column for use in affinity purification of polyvalent antibodies to the corresponding bacterium from which the polysaccharide or carbohydrate antigen was extracted, it is necessary to complex it with a protein spacer molecule suitably prepared to ensure that it will stably bond to both the polysaccharide or carbohydrate antigen and the column and will itself remain inert during the affinity purification step. A modified bovine serum albumin ("BSA") was chosen as the preferred spacer molecule and was prepared as in Example III:

EXAMPLE III

Preparation of Protein Spacer Molecule

An 0.5M aqueous solution of hydrazine dihydrochloride from Aldrich Chemical Co., Inc. (Milwaukee, Wis.) was prepared and its pH was adjusted to 5.2 with dry NaOH. The solution was then mixed with dry BSA from Sigma Chemical Co. to a final concentration of 25 mg. per ml. of BSA. After the BSA was completely dissolved. N-(dimethylaminopropyl)-$N^1$-ethylcarbodiimide hydrochloride obtained from Fluka Chemical Co. (St. Louis, Mo.) was added to a final concentration of 2.5 mg. per ml. The mixture was stirred overnight at ambient temperature and then dialyzed for a period of about five days against distilled water at 4° C., with daily changes of water.

In lieu of this modified BSA, it is contemplated that other appropriate spacer molecules may be used.

The conjugation of the O-polysaccharide antigen from serogroup 1 of *L. pneumophila* to the spacer molecule was conducted as follows:

EXAMPLE IV

Conjugation of O-polysaccharide Antigen to Spacer Molecules

*L. pneumophila* serogroup 1 essentially protein-free O-polysaccharide antigen was dissolved in distilled water in a concentration of 4-5 mg/ml and the pH was adjusted to 5.0 with 1 M HCl. The modified BSA solution prepared as in Example III was adjusted to pH 5.0 with 1 M HCl and slowly added, in a weight ratio of 4-to-1 of the O-polysaccharide antigen solution, to the latter. After 5 minutes of stirring, about 100-200 mcl of distilled water containing the N-(dimethylamino-propyl-$N^1$-ethylcarbodiimide hydrochloride referred to in Example III was added in a weight ratio of 1:2 to the O-polysaccharide antigen/BSA solution. The resulting mixture was stirred at ambient temperature overnight.

To separate the conjugate of the O-polysaccharide antigen with modified BSA from any unreacted materials present, the reaction mixture was chromatographed on a Sepharose CL-4B column equilibrated with a buffer of 0.1 M $NaH_2PO_4$: 0.5 M NaCl. All of the chromatography fractions were subjected to testing for antigen activity using the commercial Binax EIA test referred to above. All fractions that showed antigen activity in the tested were pooled in and used for affinity column preparation as shown in Example V.

EXAMPLE V

Coupling of Conjugate to Activated Chromatographic Column

An immunoadsorbent gel was prepared by conventionally activating Sepharose CL-4B with cyanogen bromide. The ligand of O-polysaccharide antigen with modified BSA, prepared as in Example IV, was coupled to it using procedures known in the art, e.g., as described in Hermanson, G. T., et al. in *Immobilized Affinity Ligand Techniques,* 53-56 (Academic Press, Inc. 1992). The gel was then packed in a column and washed successively with 5-10 volumes per volume of gel with PBS of pH 7.2, triple strength PBS of pH 7.2 and 0.2 M glycine-HCl of pH 2.5. The resulting activated column was used, as described below, for affinity purification of polyvalent antibodies to *L. pneumophila* serogroup 1 antigen. The column after elution should be stored in PBS or another neutral buffer until used.

Instead of cyanogen-bromide activated Sepharose, spherelose and various commercially available activated columns could be used in this step.

EXAMPLE VI

Affinity Purification of Antibodies

The activated column described in Example V was used for the affinity chromatography of rabbit-anti-*L. pneumophila* serogroup 1 polyvalent antibodies to *L. pneumophila* serotype antigen according to the method described by Harlow E. and Lane, D. in *Antibodies: A Laboratory Manual* at 313-315 (Cold Spring Harbor Laboratory, 1988). Elution of the antibodies from the column was effected with 0.2M glycine-HCL buffer of pH 2.5. Alternative eluants such as 3M NaSCN or 0.1M $Et_3N$ could be substituted.

These affinity-purified antibodies were utilized in an ICT test specific to *L. pneumophila* serogroup 1 as described in the following example.

EXAMPLE VII

ICT Device and its Preparation

A. Preparation of Test Device

Figure 1A:
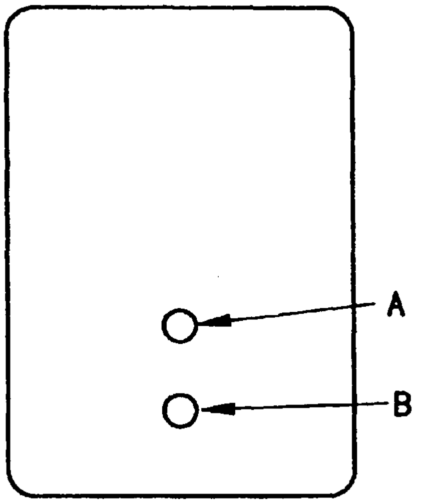

A test device comprising a hinged cardboard housing equipped with a window to allow the viewing of both the test results and control results was prepared as shown in FIG. 1. The device has a recess into which is placed a preformed plastic swab well for receiving the sample-wetted swab on the right hand (labeled 1 in the drawing). An overlabel shown in FIG. 1A is then placed over the entire right-hand side of the device. The overlabel has been equipped with two holes—a lower one (marked B on FIG. 1*a*) into which the saturated swab is to be inserted and an upper one (marked A in FIG. 1A) toward which the swab will be pushed after insertion thereof into the hole B. The position of the overlabel with its holes A and B, and swab well cooperate to hold the swab in a proper position during the assay and to promote the expulsion of sorbed liquid from the swab.

Figure 1B:
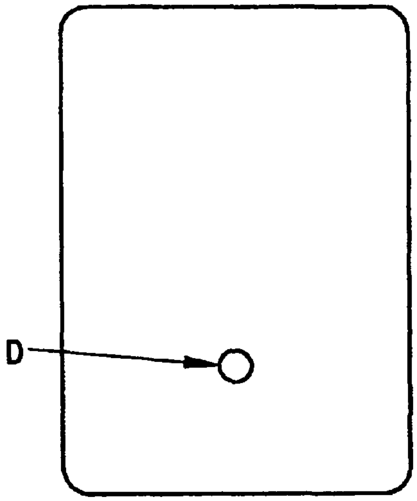

A preassembled test strip (marked C on FIG. 1) described below, is inserted into the recess (labeled 2 on FIG. 1) and held in place by an adhesive applied to the bottom thereof. An overlabel shown in FIG. 1B is placed atop the left-hand side. It has been equipped with a single hole (marked D in FIG. 1B) which mates to the right-hand side hole A when the device is closed for performance of the assay.

The assembled device is stored in a sealed pouch with desiccant until it is used. Prior to sealing the pouch and storing, a lightly adhesive tape is placed on the outer edge of the right-hand half of the device.

B. Construction and Preparation of the Preassembled Test Strip

Figure 1C:
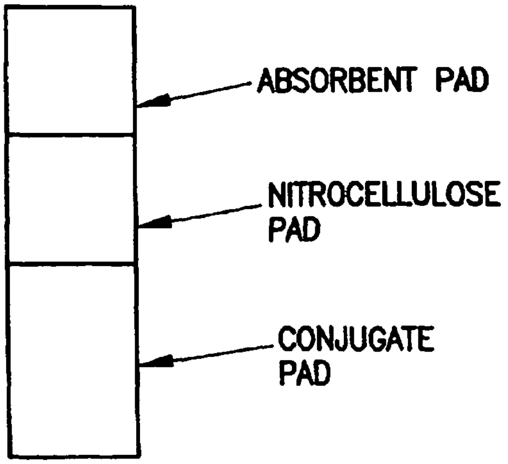

FIG. 1C shows the construction of the preassembled strip. It is comprised of a conjugate pad of sorbent material in which a conjugate of gold particles and the affinity-purified rabbit anti-*Legionella pneumophila* serogroup 1 antibodies described above have been impregnated. In contact with this pad is a nitrocellulose pad onto which capture line for the sample which reacts with the conjugate has been established by embedding a stripe of affinity-purified rabbit anti-*L. pneumophila* serogroup 1 antibodies, prepared as described above. The nitrocellulose pad also has a downstream control line established by striping the pad with goat anti-rabbit immunoglobulin (IgG). Following the nitrocellulose pad, the strip is ended by an absorbent pad which serves as a reservoir for liquid. All of these pads are backed by an adhesive strip when the device is ready to ship.

The conjugate pad is normally made from non-woven polyester or extruded cellulose acetate. To prepare this pad for use in the assay, gold particles of 50 nm. diameter are conjugated to affinity-purified rabbit anti-*Legionella pneumophila* serotype 1 antibodies prepared as described above. The conjugation is effected using a known method such as that described by DeMay in Polak, J. M. and Van Norden, S. (Eds.), *Immunochemistry: Modern Methods and Application*, (Wright, Bristol, England, 1986). The gold conjugate particles are mixed with a drying agent consisting of aqueous 5 mM sodium tetraborate of pH 8.0 containing 1.0% BSA, 0.1% Triton X-100, 2.0% Tween 20, 6.0% sucrose and 0.02% sodium azide. The pad is heated sufficiently to remove all of the liquid present and stored in a low-humidity environment pending, assembly of the test strip. These pads and their treatment are especially chosen so that the pads will hold the dry conjugate and will release it only when later wetted by sample.

The nitrocellulose pad is first treated by embedding a stripe of affinity purified rabbit anti-*L. pneumophila* serotype 1 antibodies in a first portion thereof, using a carrier solution of phosphate buffered saline. These antibodies act as the capture line. In a second portion of the pad downstream of the first one in the assembled test device, the control line is established by striping goat anti-rabbit IgG in the same carrier solution on the surface of the pad. The nitrocellulose pad is then subjected to desiccation at 18-25° C. to promote permanent absorption of the protein stripes thereto.

The absorbent pad used is of a commercially available cellulosic material sold under the name Ahlstrom 939. This pad requires no special treatment.

C. Kit Preparation

As sold in commerce, the test device containing the finished test strip is assembled. In practice, a number of devices are packaged with a commensurate number of swabs fashioned from fibrous Dacron and a bottle of "Reagent A" equipped with a top adapted to deliver Reagent A dropwise. "Reagent A" is a solution if 2.0% Tween 20, 0.05% sodium azide and 0.5% sodium dodecyl sulfate in a 0.05M sodium citrate-sodium phosphate buffer of pH 6.5. Positive and negative controls are also included in each kit.

The use of the finished test devices to identify *L. pneumophila* serogroup 1 antigen is illustrated in the following example VIII:

EXAMPLE VIII

Conducting the ICT Test for *L. pneumophila* Serogroup 1 Antigen

In practice, the swab furnished with each device is dipped into the liquid sample, completely immersing the swab head. The use of the swab to act as a filter for undissolved solids, semisolids and colloids present in liquid biological samples such as urine, blood, lymph, etc. and also in liquid environmental samples is the subject of copending application Ser. No. 09/044,677 of Norman Moore and Vincent Sy filed Mar. 19, 1998, which is assigned to Binax, Inc. The swab is inserted into the hole at the bottom of the device (hole B of FIG. 1A) and gently pushed upward so that the swab tip is visible in the top hole (hole A of FIG. 1A). The reagent A vial is held vertically above hole B and two drops of Reagent A are slowly added. The adhesive liner is then immediately peeled from the right edge of the device and the device is closed and securely sealed, thus pressing the swab in the swab well against the gold conjugate pad. After 15 minutes, the result can be read in the window of the device. A negative sample—i.e., one containing no *L. pneumophila* serogroup 1 antigen-will exhibit only the control line in the top half of the window. A positive sample containing the target antigen will show two lines, the lower one of which is the patient (or sample) line; even a faint sample line indicates the presence of the target antigen in the sample. If no line appears in the window after 15 minutes, or only a sample line appears in the lower part of the window, the test is invalid and must be repeated.

Using the procedure described above, the devices prepared as described in Example VII were tested in the ICT procedure just described against 300 patient urine samples, 100 of which had been previously diagnosed as having *L. pneumophila* serogroup 1 infection.

These ICT tests according to this invention were conducted under circumstances such that the previous diagnoses were unknown to personnel performing the ICT tests. Overall, 98% of the ICT tests agreed with the previous positive diagnoses. Also overall, 98% of the urine samples previously diagnosed as negative for *L. pneumophila* serogroup 1 O-polysaccharide antigen gave results in agreement therewith when tested by the ICT procedure described herein, using the ICT device described in Example VII.

EXAMPLE IX

Use of the ICT to Test Environmental Samples

Applicability of this same test to environmental samples suspected of containing *L. pneumophila* serogroup 1 was also investigated as follows:

Water was seeded with *L. pneumophila* serogroup 1 bacteria obtained from a commercial source. The mixture was concentrated by filtering through a 0.22 μm filter. A swab dipped in the sample was applied to the device, the device was closed and the assay was allowed to proceed. A positive result was observed within less than 15 minutes.

EXAMPLE X

Western Blot Immunoassay for Detection of Cross-Reactive Carbohydrate Antigens of *L. Pneumophila* Serogroups 1, 2, 4 and 5

In order to perform the Western Blot immunoassay using a kit purchased from Bio-Rad Laboratories, *L. pneumophila* serogroup 5 cells were cultured as in Example H. A suspension of these cells was solubilized with 1% sodium dodecylsulfate in the presence of 10 mM mercaptoethanol at 100° C. for 5 minutes. The solubilized cells were treated with protease K and then subjected to electrophoretic separation of protein according to standard procedures provided by Bio-Rad.

The carbohydrate antigen from *L. pneumophila* serogroup 5 was conjugated to the spacer molecule described in Example III hereof in the manner described in Example IV and applied to an activated Sepharose column as described in Example V. This column was then used for the affinity purification of polyvalent rabbit antibodies specific to the carbohydrate antigen of *L. pneumophila* serogroup 5 (which were conventionally obtained from serum of a rabbit previously injected with the protein-containing of *L. pneumophila* serogroup 5) using the procedure of Example VI.

Figure 2:
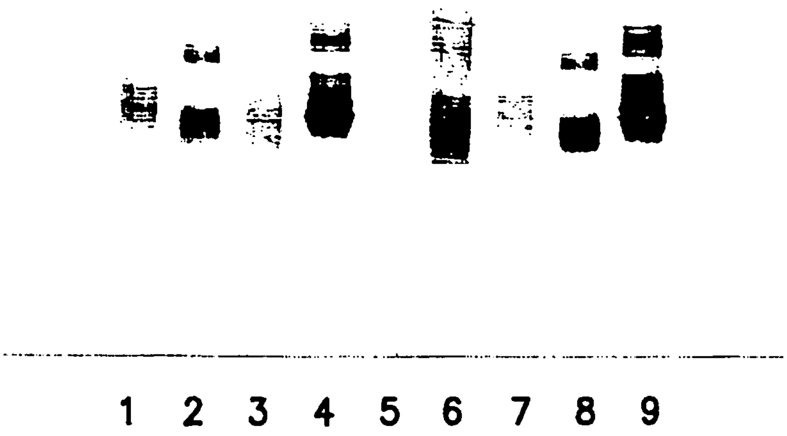
FIG. 2 hereof shows the results of Western blot analyses of phosphate-buffered saline extracts of *L. pneumophila* serogroups 1, 2, 4 and 5 with *L. pneumophila* serogroup 5, essentially protein-free carbohydrate antigen-affinity-purified polyclonal antibody specific to serogroup 5 antigen, which analysis is described in Example X hereof.

The Western immunoblot analysis was performed using a reagent kit from Bio-Rad and according to directions from this manufacturer. Briefly, the PBS extract of cells of *L. pneumophila* antigens 1, 2, 4 and 5 was subjected to the SDS-PAGE in 12% polyacrylamide gel blocked with 1% BSA with PBS transferred onto a nitrocellulose membrane. After this step, the membrane was incubated with affinity purified antibodies specific to carbohydrate of *L. pneumophila* serogroup 5. The membrane, washed as recommended by the manufacturer, and incubated with horseradish peroxidase conjugated to goat-anti-rabbit antibodies provided by Bio-Rad. After washing, the membrane was developed with a substrate system of 0.022 M 4-chloro-1 naphthol and 0.0012 M N; N-dimethyl-p-phenylene-diamine monohydrochloride in 0.1 M sodium citrate buffer of pH 6.9 containing 2.9 mM of hydrogen peroxide. FIG. 2 hereof shows the Western blot assay results compared with that of the prestained SDS-PAGE standard (in Lane 5) for the affinity purified antibodies of serogroup 5 of *L. pneumophila* against PBS extracts containing antigens of *L. pneumophila* as follows:

Lanes 1 and 7—*L. pneumophila* serogroup 2 (strain Togus-1)

Lanes 2 and 8—*L. pneumophila* serogroup 4 (strain Los Angeles-1)

Lanes 3 and 6—*L. pneumophila* serogroup 1 (strain Philadelphia-1)

Lanes 4 and 9—*L. pneumophila* serogroup 5 (strain U8W).

It is pointed out that the affinity purified antibodies for Lanes 1-4 were affinity purified on a column to which carbohydrate antigen from *L. pneumophila* serogroup 5 (strain U8W) was attached while those for Lanes 6-9 were affinity purified in the same manner on a column having attached carbohydrate antigen of *L. pneumophila* serogroup 5 (strain Dallas IE).

FIG. 2 clearly demonstrates that affinity purified antibodies as herein disclosed of *L. pneumophila* serogroup 5 react with antigens of *L. pneumophila* serogroups 1, 2, and 4 in addition to those of serogroup 5.

An ICT assay as described above in which affinity purified antibodies from *L. pneumophila* serogroup 5 are substituted for affinity purified antibodies from *L. pneumophila* serogroup 1 is contemplated.

Those skilled in the art of immunochemistry generally, and especially those skilled in immunoassays, will recognize that other materials and ingredients and at times, other procedural steps, can readily be substituted for those specifically recommended herein. A vast array of literature, both patent and non-patent, discusses the design and use of reliable, one-time-use, disposable immunoassay test devices that could be substituted for the preferred ICT device described and recommended herein. It is not intended that the present invention should be limited with respect to substitutable assay devices, materials, ingredients or process steps except insofar as the following claims may so limit it.

What is claimed is:

1. A device for determining the presence of *Legionella pneumophila* serogroup 1 in a liquid sample, the device comprising:

a porous test strip comprising a sample receiving zone;

multiple binding agents, each binding agent comprising:

antigen specific affinity-purified polyclonal antibodies conjugated to a detectable particle, wherein the antigen specific affinity-purified polyclonal antibodies specifically bind a *Legionella pneumophila* serogroup 1 O-polysaccharide antigen and wherein the binding agents are essentially free of antibodies that bind proteins of *Legionella pneumophila* serogroup 1 O-polysaccharide;

multiple capture agents; and a capture zone;

wherein the porous test strip defines a liquid flow path extending downstream from the sample receiving zone and along which liquid received by the sample receiving zone can pass at least to the capture zone, the binding agents are disposed in a dried state along the flow path of the test strip downstream from the sample receiving zone and upstream from the capture zone, the binding agents are mobilizable by liquid passing along the flow path, and the capture agents are disposed in the capture zone and are each capable, in the presence of *Legionella pneumophila* serogroup 1 in a liquid sample received by the sample receiving zone, of binding a complex comprising one of the binding agents bound to the antigen.

2. The device of claim 1, wherein the capture agents are antibodies.

3. The device of claim 2, wherein the capture agents are polyclonal antibodies.

4. The device of claim 1, wherein the detectable particle is a color-producing particle.

5. The device of claim 3, wherein the detectable particle is colloidal gold.

6. The device of claim 1, wherein the detectable particle is a color-producing particle and the capture agents are antibodies.

7. The device of claim 1, wherein the presence of *Legionella pneumophila* serogroup 1 in a liquid sample is determined within fifteen minutes of applying the liquid sample to the device.

* * * * *